US00PP12238P2

(12) United States Plant Patent
Gray

(10) Patent No.: US PP12,238 P2
(45) Date of Patent: Nov. 27, 2001

(54) MANDEVILLA PLANT NAMED 'RED VELVET'

(75) Inventor: John F. Gray, Hawthorne, FL (US)

(73) Assignee: Lake Area Nursery, Hawthorne, FL (US)

( * ) Notice: Subject to any disclaimer, the term of this patent is extended or adjusted under 35 U.S.C. 154(b) by 0 days.

(21) Appl. No.: 09/664,134

(22) Filed: Sep. 19, 2000

(51) Int. Cl.[7] ..... A01H 5/00
(52) U.S. Cl. ..... Plt./232

(58) Field of Search ..... Plt./232

*Primary Examiner*—Bruce R. Campell
*Assistant Examiner*—June Hwu
(74) *Attorney, Agent, or Firm*—C. A. Whealy

(57) ABSTRACT

A distinct cultivar of Mandevilla plant named 'Red Velvet', characterized by its vigorous growth habit; rapid growth rate; large, glossy, dark green leaves; large flowers that are dark pink in color when temperatures are less than 29° C. and intensify to dark red in color when temperatures are greater than 29° C.; red flower throat color; and tolerance to low and high temperatures.

2 Drawing Sheets

BACKGROUND OF THE INVENTION

The present Invention relates to a new and distinct cultivar of Mandevilla plant, botanically known as *Mandevilla hybrid*, and hereinafter referred to by the cultivar name Red Velvet.

The new cultivar is a product of a planned breeding program conducted by the Inventor in Hawthorne, Fla. The objective of the breeding program was to develop new vigorous Mandevilla cultivars with attractive and unique flower colors.

The new cultivar originated from a self-pollination of the cultivar PSJAM LP1, disclosed in U.S. Plant Pat. No. 10,611, made in Hawthorne, Fla., in November, 1996. The new cultivar was discovered and selected by the Inventor as a flowering plant within the progeny from this self-pollination in a controlled environment in Hawthorne, Fla., in 1999. The new cultivar was selected on the basis of its large dark red flowers and vigorous growth habit.

Asexual reproduction of the new cultivar by terminal cuttings taken in Hawthorne, Fla., since April, 1999, has shown that the unique features of this new Mandevilla are stable and reproduced true to type in successive generations.

SUMMARY OF THE INVENTION

Plants of the cultivar Red Velvet have not been observed under all possible environmental conditions. The phenotype may vary somewhat with variations in environment such as temperature, light intensity, daylength, humidity, water status and/or fertilizer rate and type without, however, any variance in genotype.

The following traits have been repeatedly observed and are determined to be the unique characteristics of 'Red Velvet'. These characteristics in combination distinguish 'Red Velvet' as a new and distinct cultivar:

1. Vigorous growth habit and rapid growth rate.
2. Large, glossy, dark green leaves.
3. Large flowers that are dark pink in color when temperatures are less than 29° C. and intensify to dark red in color when temperatures are greater than 29° C.
4. Red flower throat color.
5. Tolerance to low and high temperatures.

Plants of the new Mandevilla differ primarily from plants of the parent cultivar PSJAM LP1 in flower color as flowers of plants of the cultivar PSJAM LP1 are light pink in color.

Plants of the new Mandevilla can be compared to plants of the cultivar PSJAM DP1, disclosed in U.S. Plant Pat. No. 10,413. In side-by-side comparisons conducted by the Inventor in Hawthorne, Fla., plants of the new Mandevilla were more vigorous, grew faster and had darker colored flowers than plants of the cultivar PSJAM DP1.

Plants of the new Mandevilla can be compared to plants of the cultivar Ruby Star, disclosed in U.S. Plant Pat. No. 8,842. In side-by-side comparisons conducted by the Inventor in Hawthorne, Fla., plants of the new Mandevilla were much faster growing, produced three to four times as many flowers per plant, and had larger flowers than plants of the cultivar Ruby Star. In addition, flowers of the new Mandevilla have overlapping petals whereas flowers of the cultivar Ruby Star do not have overlapping petals.

Plants of the new Mandevilla can be compared to plants of the cultivar Alice DuPont, not patented. In side-by-side comparisons conducted by the Inventor in Hawthorne, Fla., plants of the new Mandevilla were much faster growing, produced three to four times as many flowers per plant, and had larger and darker colored flowers than plants of the cultivar Alice DuPont.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Mandevilla.

The photograph on the first sheet comprises a side perspective view of a typical plant of 'Red Velvet' grown on a lattice.

The photograph at the top of the second sheet comprises a close-up view of typical flowers and leaves of 'Red Velvet'.

The photograph at the bottom of the second sheet comprises a close-up view of typical flowers from plants of 'Red Velvet', 'PSJAM DP1', 'Alice DuPont' and 'Ruby Star', left to right.

DETAILED BOTANICAL DESCRIPTION

In the following description, color references are made to The Royal Horticultural Society Colour Chart except where general terms of ordinary dictionary significance are used. Plants used for this description were about six months old and grown in one-gallon containers in a clear polyethylene-covered greenhouse in Hawthorne, Fla. during the spring. Day temperatures ranged from 29 to 35° C. and night temperatures ranged from 13 to 18° C.

Botanical classification: Mandevilla hybrid cultivar Red Velvet.

Parentage: Self-pollination of Mandevilla hybrid cultivar PSJAM LP1, disclosed in U.S. Plant Pat. No. 10,611.

Propagation:

*Type cutting.*—Terminal cuttings.

*Time to initiate roots, summer.*—About 20 days at 32° C.

*Time to initiate roots, winter.*—About 30 days at 24° C.

*Time to develop roots, summer.*—About 45 days at 32° C.

*Time to develop roots, winter.*—About 60 days at 24° C.

*Root description.*—Numerous, thick, fibrous and freely branching.

Plant description:

*Form.*—Perennial evergreen flowering plant; twining vine; initially upright, then vining, requires support to maintain upright habit. Plants are typically pinched about 3 months after planting to enhance lateral branch development.

*Crop time.*—Relatively rapid growth rate, from rooted cuttings, about 6 months are required to produce finished flowering plants in one-gallon containers.

*Plant height* (*length*).—About 82 cm.

*Plant diameter.*—About 37 cm.

*Vigor.*—Vigorous.

*Lateral branches.*—Length: About 75 cm. Diameter: About 5.5 mm. Internode length: About 11 cm. Shape: Round in cross-section. Aspect: Initially upright, then trailing, requires support. Strength: Flexible, but strong. Texture: Pubescent; very fine and dense white hairs. Color: Initially green, 144A, then becoming dark purple red, close to 187B; woody, brown, 165A; becoming brown, 165A, with dark purple red, 187A, tones.

*Foliage description.*—Leaves large, simple, generally symmetrical and long-persisting; opposite. Length: About 18.5 cm. Width: About 9.3 cm. Shape: Oblong. Apex: Acuminate to aristate. Base: Shallow cordate, lobes overlapping. Margin: Entire. Texture/luster: Rugose, leathery, durable; upper surface, glossy; lower surface, dull with very fine pubescence. Petiole length: About 8 mm. Petiole diameter: About 4.5 mm. Color: Young foliage, upper surface: More green than 147A. Young foliage, lower surface: More green than 147B. Mature foliage, upper surface: Much darker and more green than 147A. Mature foliage, lower surface: Close to 147B. Veins, upper surface: Close to 147B. Veins, lower surface: Close to 144B. Petiole: 144B to 144C.

Flower description:

*Flower type and habit.*—Large salverform flowers arranged in terminal and axillary racemes; indeterminate; flowers face mostly outward of upright. Flowers self-cleaning. Very freely flowering with potentially more than 60 flowers per plant.

*Natural flowering season.*—Spring until frost in the autumn; flowering continuous.

*Flower longevity on the plant.*—About one week.

*Fragrance.*—None detected.

*Inflorescence diameter.*—About 26 cm.

*Inflorescence depth.*—About 21 cm.

*Flowers.*—Appearance: Flared trumpet, corolla fused, five-parted; flowers star-shaped; iridescent. Diameter: About 12.75 cm. Depth (length): About 7.5 cm. Corolla tube length: About 6.6 cm. Throat diameter: About 2.8 cm.

*Flower buds* (*just before opening*).—Length: About 9.2 mm. Diameter: About 2 cm. Shape: Oblong. Color: 58B.

*Corolla.*—Arrangement/appearance: Single whorl of five petals, fused into flared trumpet; overlapping. Petal length from throat: About 5.5 cm. Petal width: About 6.5 cm. Petal shape: Spatulate. Petal apex: Rounded. Petal margin: Entire; finely undulate. Petal texture: Smooth, velvety. Color: Flowers are dark pink in color when temperatures are less than 29° C. and intensify to dark red in color when temperatures are greater than 29° C. Petal, upper surface, when opening: Pink, close to 58C to 58B. Petal, lower surface, when opening: Pink, close to 58D to 58C. Petal, upper surface, about three days after opening: At temperatures less than 29° C.: Dark pink, close to 58B or darker than 58B. At temperatures greater than 29° C.: Dark red, 53B to 53D, with dark red, 46A to 53A, overtones; becoming more red, 46A, with development. Petal, lower surface, about three days after opening: At temperatures less than 29° C.: Dark pink, close to 58B to 58C. At temperatures greater than 29° C.: Dark red, close to 53B to 53D; becoming more red, 46A, with development. Tube, fully opened: 53B to 53D to close to 60B or slightly lighter than 60B; becoming more red, 46A, with development. Throat, fully opened: 53B to 53D to close to 60B or slightly lighter than 60B; towards base, faint white streaks; base, yellow, close to 7A.

*Sepals.*—Arrangement/appearance: Five per flower; fused, campanulate. Calyx length: About 1.25 cm. Calyx width: About 5 mm. Shape: Elongated, linear. Apex: Sharply acute. Margin: Entire. Texture: Smooth, slightly waxy. Color: Upper surface: 144B with red, 53A, towards apex. Lower surface: 144B with red, 53A, towards apex.

*Peduncles.*—Length: About 24 cm. Diameter: About 4 mm. Angle: Mostly erect; zig-zag. Strength: Flexible, but strong. Color: 144A.

*Pedicels.*—Length: About 2.7 cm. Diameter: About 3 mm. Angle: Erect. Strength: Flexible, but strong. Color: Initially green, 144A, then becoming dark red, 53A, with development.

*Reproductive organs.*—Stamens: Quantity: Five; filaments fused to corolla. Anther shape: Oblong, elongated. Anther size: About 6 mm by 1.5 mm. Anther color: Close to 5D. Pollen: None observed. Pistils: Quantity: One. Pistil length: About 1.2 cm. Stigma color: 144B. Style color: 144B to almost white. Ovary color: 144A.

*Seed.*—Seed production has not been observed.

Disease/pest resistance: Plants of the new Mandevilla have not been noted to be resistant to pathogens or pests common to Mandevilla.

Weather tolerance: Plants of the new Mandevilla have been observed to be tolerant to rain and wind and tolerant to temperatures from 0 to higher than 43° C.

It is claimed:

1. A new and distinct cultivar of Mandevilla plant named 'Red Velvet', as illustrated and described.

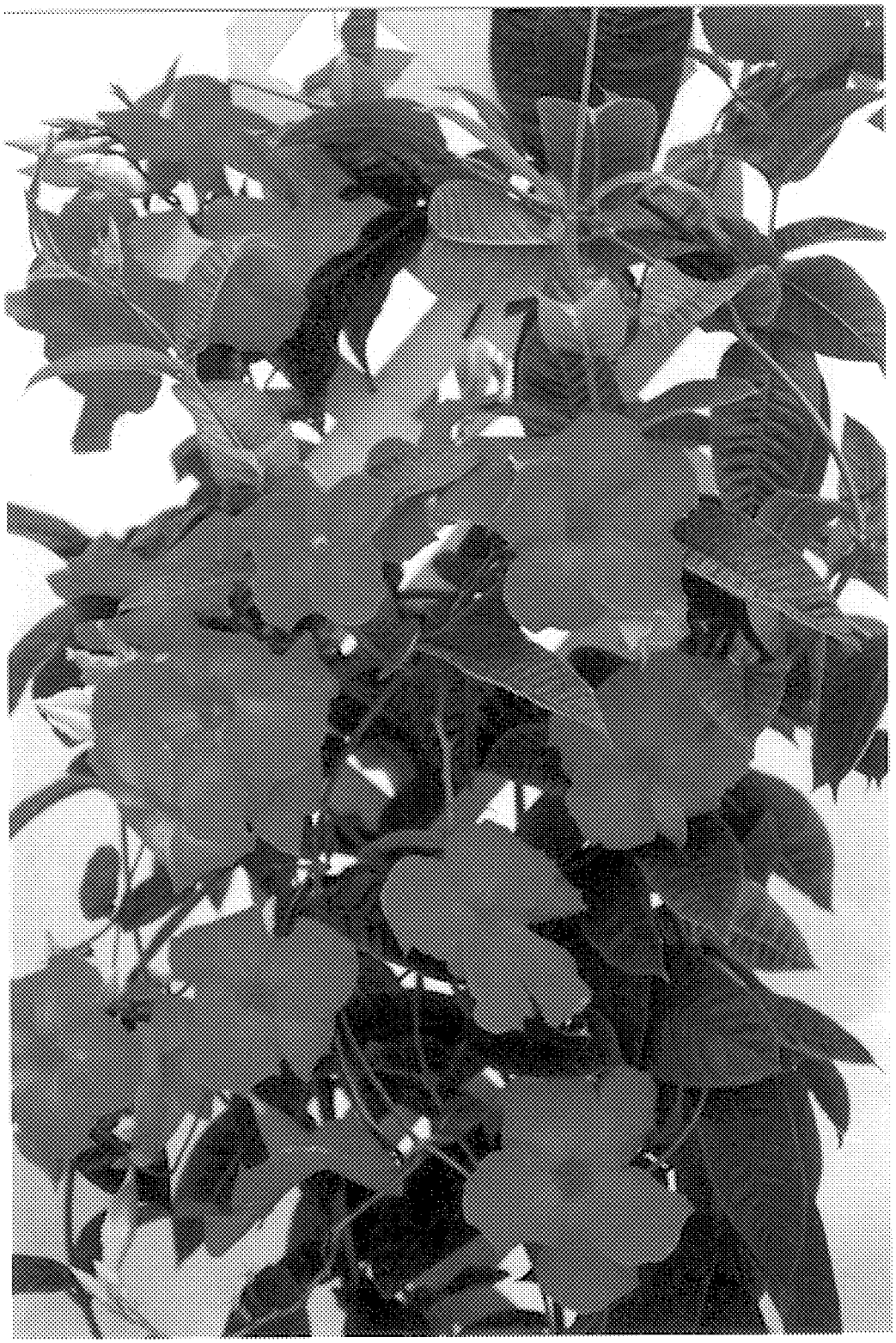

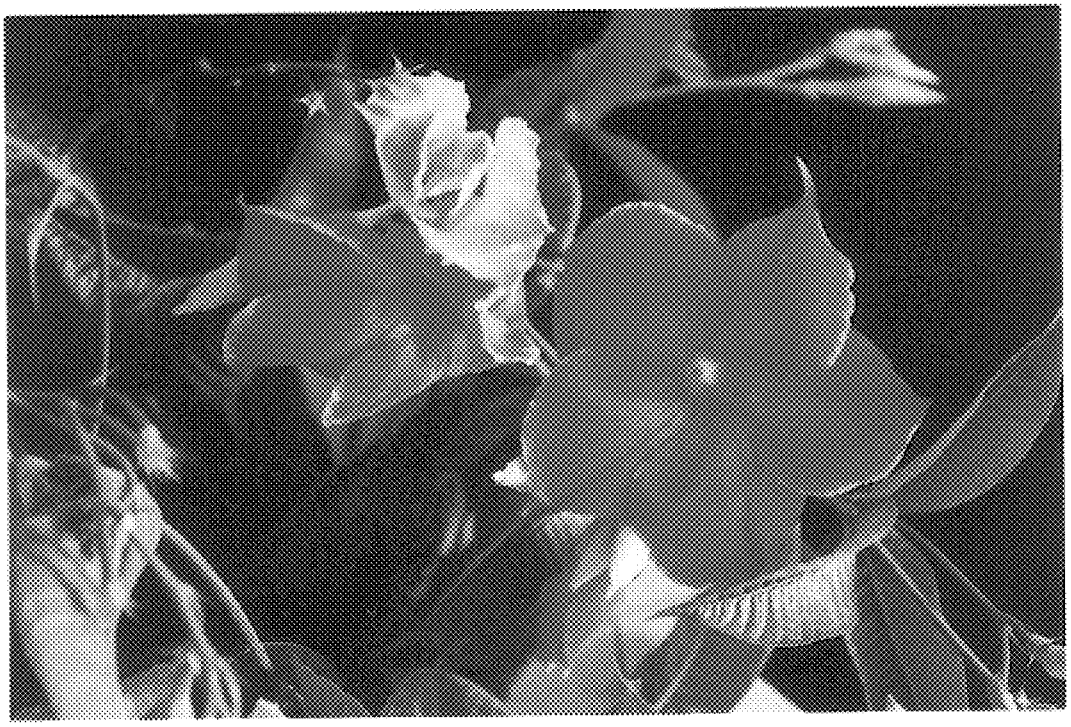
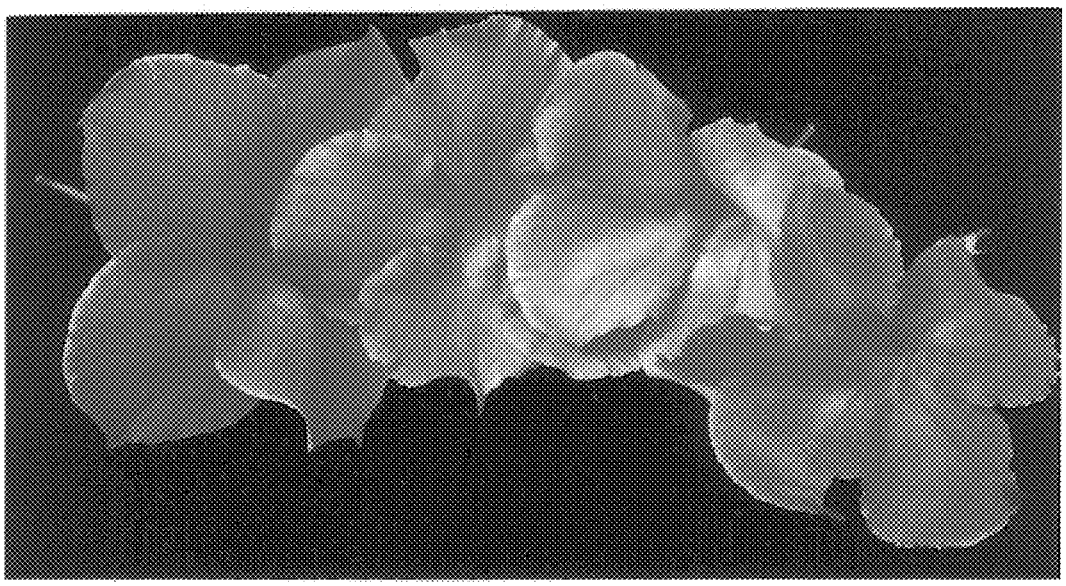

* * * * *